(12) United States Patent
Cowden et al.

(10) Patent No.: US 6,638,916 B1
(45) Date of Patent: Oct. 28, 2003

(54) USE OF SULFATED OLIGOSACCHARIDES AS INHIBITORS OF CARDIOVASCULAR DISEASE

(75) Inventors: William B. Cowden, Kambah (AU); Douglas J. Francis, Garran (AU); Christopher R. Parish, Campbell (AU)

(73) Assignee: The Australian National University, Acton (AU)

( * ) Notice: Subject to any disclaimer, the term of this patent is extended or adjusted under 35 U.S.C. 154(b) by 0 days.

(21) Appl. No.: 09/486,617

(22) PCT Filed: Sep. 1, 1998

(86) PCT No.: PCT/AU98/00707

§ 371 (c)(1),
(2), (4) Date: May 9, 2000

(87) PCT Pub. No.: WO99/11273

PCT Pub. Date: Mar. 11, 1999

(30) Foreign Application Priority Data

Sep. 1, 1997 (AU) .............................................. PO8884

(51) Int. Cl.$^7$ ......................... A61K 31/715; C07H 3/06
(52) U.S. Cl. ........................ 514/54; 514/61; 536/122; 536/123; 536/123.1
(58) Field of Search .................... 514/54, 61; 536/122, 536/123, 123.1

(56) References Cited

U.S. PATENT DOCUMENTS

| | | | |
|---|---|---|---|
| 4,933,326 A | 6/1990 | Bianchini et al. .............. | 514/56 |
| 5,464,827 A | 11/1995 | Soll ............................ | 514/58 |
| 5,587,364 A | * 12/1996 | McAnalley et al. .......... | 514/54 |
| 5,993,797 A | * 11/1999 | Kitazato et al. ............ | 424/78.3 |

FOREIGN PATENT DOCUMENTS

| | | |
|---|---|---|
| AU | A 10397/83 | 7/1983 |
| AU | B 12127/92 | 9/1992 |
| AU | B 60524/94 | 10/1994 |
| EP | 0208623 | 1/1987 |
| EP | 0485748 | 5/1992 |
| WO | WO 84/01777 | 5/1984 |
| WO | WO 92/18546 | 10/1992 |
| WO | WO 93/05075 | 3/1993 |
| WO | WO 93/09790 | 5/1993 |
| WO | WO 95/33468 | 12/1995 |
| WO | WO 96/09828 | 4/1996 |
| WO | WO 96/33726 A1 * | 10/1996 |

OTHER PUBLICATIONS

Zavoral et al. Am. J. Clinical Nutrition, Aug. 1983, 38(2), 285–94. Medline Abstact Only, AN 83279860.*

Pukac et al., "Antiproliferative Effects of Novel, Nonanticoagulant Heparin Derivatives on Vascular Smooth Muslce Cells In Vitro and In Vivo", American Journal of Pathology, vol. 139 No. 6, Dec. 1991.

* cited by examiner

Primary Examiner—James O. Wilson
Assistant Examiner—Leigh C. Maier
(74) Attorney, Agent, or Firm—Fulwider Patton Lee & Utecht, LLP

(57) ABSTRACT

A method for the inhibition of vascular smooth muscle cell hyperplasia in a human or other warm-blooded animal patient in need of such treatment, comprises administration to the patient of an effective amount of at least one sulfated oligosaccharide, wherein the oligosaccharide has the general formula I:

$$R_1-(R_x)_n-R_2 \qquad (I)$$

wherein $R_1$ and $R_2$ and each $R_x$ represents a monosaccharide unit, all of which may be the same or different, adjacent monosaccharide units being linked by $1\rightarrow2$, $1\rightarrow3$, $1\rightarrow4$ and/or $1\rightarrow6$ glycosidic bonds and n is an integer of from 1 to 6.

5 Claims, 3 Drawing Sheets

USE OF SULFATED OLIGOSACCHARIDES AS INHIBITORS OF CARDIOVASCULAR DISEASE

This is a National Stage entry under 35 USC 371 of PCT/AU98/00707, filed Sep. 1, 1998.

FIELD OF THE INVENTION

This invention relates to sulfated oligosaccharides, and in particular to the use of certain sulfated oligosaccharides as inhibitors of vascular smooth muscle cell hyperplasia, particularly in the treatment of atherosclerosis and restenosis after coronary angioplasty.

BACKGROUND OF THE INVENTION

The normal artery wall consists of luminal surface covered by a unicellular layer of endothelial cells and a subluminal multicellular layer of smooth muscle cells embedded in a complex extracellular matrix (ECM). A major component of the ECM is the glycosaminoglycan, heparan sulfate, which is believed to normally inhibit smooth muscle cell proliferation[1-3]. In contrast, atherogenesis is associated with a loss of ECM heparan sulfate with a consequent migration and proliferation of smooth muscle cells[1-3]. The factors which initiate ECM degradation are poorly understood, although it has been suggested that heparanase produced by leukocytes infiltrating the developing atherosclerotic plaque may result in the loss of ECM heparan sulfate[4].

The treatment of narrow and occluded coronary arteries in atherosclerosis frequently involves dilatation by balloon angioplasty. Unfortunately, in approximately 30% to 40% of patients restenosis occurs due to vascular hyperplasia, a process which is believed to result from the denudation of vessel endothelium and the subsequent migration and proliferation of subendothelial smooth muscle cells[5]. As with atherogenesis, heparanase-mediated loss of ECM heparan sulfate is believed to be a critical factor in angioplasty-associated restenosis[1-2].

Prior International Patent Application No. PCT/AU96/00238 discloses the preparation of a class of sulfated oligosaccharides, based on polymers of monosaccharide units linked by 1→2, 1→3, 1→4 and/or 1→6 glycosidic bonds and consisting of from 3 to 8 monosaccharide units, which are potent inhibitors of mammalian heparanases and can be used to inhibit human angiogenesis, tumour metastasis and inflammation.

In work leading to the present invention, it has been shown that these sulfated oligosaccharides may also be used to inhibit the vascular smooth muscle cell hyperplasia associated with angioplasty-associated restenosis and atherosclerosis.

SUMMARY OF THE INVENTION

In accordance with one aspect, the present invention provides a method for the inhibition of vascular smooth muscle cell hyperplasia, and particularly for the treatment of atherosclerosis or angioplasty-associated restenosis, in a human or other warm blooded animal patient in need of such treatment, which comprises administration to the patient of an effective amount of at least one sulfated oligosaccharide, wherein the oligosaccharide has the general formula I:

$$R_1-(R_x)_n-R_2 \qquad (I)$$

wherein $R_1$ and $R_2$ and each $R_x$ represents a monosaccharide unit, all of which may be the same or different, adjacent monosaccharide units being linked by 1→2, 1→3, 1→4 and/or 1→6 glycosidic bonds; and n is an integer of from 1 to 6, preferably 3 or 4.

Preferably, the sulfated oligosaccharides have the general formula II:

$$Rx-(Rx)_n-Rx \qquad (II)$$

wherein Rx represents the same monosaccharide unit, adjacent monosaccharide units being linked by 1→2, 1→3, 1→4 and/or 1→6 glycosidic bonds, and n is an integer of from 1 to 5, preferably 3 or 4.

As used herein, the terms "inhibition of vascular smooth muscle cell hyperplasia" and "treatment of atherosclerosis or angioplasty-associated restenosis" are intended to encompass both prophylactic and therapeutic treatment of a patient in need of such treatment.

As well as being potent heparanase inhibitors, a further advantage of the sulfated oligosaccharides described above is that they have two additional effects. First, they are effective inhibitors of angiogenesis, probably by interfering with the action of heparan sulfate-binding growth factors (disclosed in prior International Patent Application No. PCT/AU96/00238) and, second, they possess unique anticoagulant/antithrombotic activity (disclosed in prior International Patent Application No. PCT/AU98/00151). Since angiogenesis is an important feature of coronary atherosclerotic plaque formation[6] and intravascular thrombus formation is a major risk factor associated with angioplasty and atherosclerosis[7], these two additional activities of the sulfated oligosaccharides further enhance their therapeutic potential.

DETAILED DESCRIPTION OF THE INVENTION

The sulfated oligosaccharides which are used in accordance with this invention are based on polymers of monosaccharide units, which may be linked by 1→2, 1→3, 1→4 and/or 1→6 glycosidic bonds and which may consist of from 3 to 8 monosaccharide units. Preferably, the oligosaccharides consist of from 3 to 6 monosaccharide units (that is n is from 1 to 4), more preferably from 5 to 6 monosaccharide units (n is from 3 to 4). The polymers may comprise homopolymers containing only one type of monosaccharide unit, or heteropolymers containing two or more different types of monosaccharide units, although homopolymers are preferred.

The monosaccharide units which are linked together to form the oligosaccharides are preferably hexoses, such as mannose, altrose, allose, talose, galactose, idose, or gulose. Particularly preferred hexoses are mannose and galactose. The hexoses may be in either the D- or the L-configuration.

The oligosaccharides of general formulae I and II also include compounds wherein the monosaccharide units are derivatised, in particular where the units are phosphate, acetyl or other ester derivatives of monosaccharides.

In general, the sulfated oligosaccharides of this invention may be prepared by sulfation of oligosaccharides by methods known per se in the art to give their corresponding O-sulfated derivatives. Suitable sulfation methods are described in International Patent Application No. PCT/AU96/00238, the contents of which are incorporated by reference. The oligosaccharides to be sulfated may be naturally occurring products including oligosaccharides occurring naturally as well as oligosaccharides prepared by enzymatic or chemical degradation of naturally occurring polysaccharides (such as mannan and a phosphomannan exopolysaccharide from the yeast *Pichia holstii*). Alternatively, the oligosaccharides may be prepared synthetically by the process disclosed in International Patent Application No. PCT/AU96/00238.

The present invention extends to the use of at least one sulfated oligosaccharide as described above in inhibition of vascular smooth muscle cell hyperplasia, and particularly in treatment of atherosclerosis on angioplasty-associated restenosis, in a human or other warm-blooded animal patient in need of such treatment.

The invention also extends to the use of at least one sulfated oligosaccharide as described above in the manufacture of a medicament for the inhibition of vascular smooth muscle cell hyperplasia, and particularly for the treatment of atherosclerosis or angioplasty-associated restenosis, in a human or other warm-blooded animal patient.

Furthermore, this invention also provides a pharmaceutical or veterinary composition for inhibition of vascular smooth muscle cell hyperplasia and particularly for treatment of atherosclerosis or angioplasty-associated restenosis, which comprises at least one sulfated oligosaccharide as described above, together with a pharmaceutically and veterinarily acceptable carrier or diluent therefor.

The active component is administered in therapeutically effective amounts. A therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

The formulation of therapeutic compositions is well known to persons skilled in this field. Suitable pharmaceutically or veterinarily acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically and veterinarily active substances is well known in the art, and it is described, by way of example, in *Remington's Pharmaceutical Sciences,* 18th Edition, Mack Publishing Company, Pennsylvania, USA. Except insofar as any conventional media or agent is incompatible with the active ingredient, use thereof in the pharmaceutical and veterinary compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human or animal subjects to be treated; each unit containing a predetermined quantity of active ingredient calculated to produce the desired therapeutic effect in association with the required pharmaceutical or veterinary carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

A variety of administration routes are available, although oral delivery is preferred because of the convenience to the patient. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

Compositions of the present invention suitable for oral administration may be presented as discrete units such as capsules, cachets, tablets or lozenges, each containing a predetermined amount of the active component, in liposomes or as a solution or suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol and lactic acid. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system can be used, some of which are adapted for implantation.

As previously described, in accordance with particularly preferred aspects of this invention, the sulfated oligosaccharides may be used in treatment of atherosclerosis and restenosis after coronary angioplasty.

Throughout this specification, unless the context requires otherwise, the word "comprise", or variations such as "comprises" or "comprising", will be understood to imply the inclusion of a stated integer or group of integers but not the exclusion of any other integer or group of integers.

Further features of the present invention are more fully described in the following Example(s). It is to be understood, however, that this detailed description is included solely for the purposes of exemplifying the present invention, and should not be understood in any way as a restriction on the broad description of the invention as set out above.

In the accompanying drawings.

Figure 3:

FIG. 3 shows a light microscope view of a haematoxylin and eosin stain of a transverse section of the carotid artery from a rat 14 days after denuding the arterial endothelial cells by saponin. In this case, the animal was treated from days 1 to 14 with 35 mg/kg/day of sulfated mannopentaose phosphate, the compound being delivered by a miniosmotic pump. Note the substantial reduction in smooth muscle cell hyperplasia compared with the untreated control depicted in FIG. 1. The material staining in the vessel lumen is a blood clot.

EXAMPLE 1
Preparation of Sulfated Oligosaccharides

Two sources of oligosaccharides may be used for subsequent sulfation. The first source represents oligosaccharides derived from naturally occurring polysaccharides. The usual preparation procedure involves partial depolymerisation of the polysaccharides by enzymatic or chemical means and size fractionation of the resultant oligosaccharides. Examples of polysaccharides from which oligosaccharides may be generated are mannan and a phosphomannan exopolysaccharide from the yeast *Pichia holstii*. The second source represents totally synthetic hexose-containing oligosaccharides prepared by chemical polymerisation of hexose monomers. Prior International Patent Application No. PCT/AU96/00238 discloses a method for the manufacture of these totally synthetic oligosaccharides. This International patent application also describes a procedure for the isolation of a mannopentaose phosphate of the structure P-6-Man-$\alpha$-(1→3)-Man-$\alpha$-(1→3)-Man-$\alpha$-(1→3)-Man-$\alpha$-(1→2)Man from the exopolysaccharide of the yeast *Pichia holstii*. The other naturally occurring oligosaccharides may be purchased commercially, for example from Seikagaku, Tokyo, Japan. Finally, all of the oligosaccharides may be sulfated by a procedure disclosed in International Patent Application No. PCT/AU96/00238, the contents of which are incorporated herein by reference.

EXAMPLE 2
Use of Sulfated Oligosaccharides to Inhibit Vascular Smooth Muscle Hyperplasia
Materials and Methods
Sulfated Oligosaccharide A mannopentaose phosphate from the exopolysaccharide of the yeast *Pichia holstii* was isolated and sulfated by the procedure disclosed in International Patent Application No. PCT/AU96/00238.

Vascular Hyperplasia Model

In order to induce vascular hyperplasia two procedures were used. In the first procedure, male Fisher 344 rats (18→30 weeks of age) were anaesthetised and approximately a 1 cm length of one of the carotid arteries exteriorised by dissection. The 1 cm arterial segment was clamped at both ends with padded artery clamps. A small volume of saponin solution (0.5 mg/ml in PBS) was injected, via a 30 gauge needle, into the arterial segment, left for 2 min and then withdrawn by suction. The 1 cm arterial section was ligated (5/0 silk) on each side of the needle hole and the arterial clamps removed, the artery reinteriorised and the wound sutured. On the following day animals were divided into control and treatment groups. The treatment group received the sulfated oligosaccharide, sulfated mannopentaose phosphate (PI-88) at a dose of 35 mg/kg/day for the next 14 days delivered via subcutaneously implanted miniosmotic pumps (Alzet 2ML2). Control animals were given the miniosmotic pumps containing saline. After 2 weeks the animals were anaesthetised (pentobarbitone), perfused with 10% buffered formalin for 20 minutes, euthanised (Pentobarbitone) and the denuded arterial segments were removed and processed for histological examination. The degree of intimal hyperplasia was determined using digital image analysis.

In the second procedure, a traditional balloon dilation model, based essentially on the method described by Clowes et al.[8] was used. Thirteen male Wistar rats (16–20 weeks of age) were anaesthetised (avertin) and the left common carotid artery exteriorised via a ventral midline incision. A padded vascular clamp was applied to the most caudal end of the exteriorised artery. Following arteriotomy a 2 F Fogarty balloon catheter was inserted into the carotid artery, the vascular clamp removed and the catheter advanced 1–1.5 cm in a caudal direction. The balloon was inflated using a 0.12 cc of air and the catheter was withdrawn to the point of arterial insertion. The balloon was then deflated and this procedure was repeated twice more. On the third withdrawal the balloon was deflated, the catheter removed from the artery and simultaneously a padded vascular clamp applied immediately caudal to the arteriotomy but leaving room for the subsequent application of a ligature (5/0 silk). A similar ligature was applied immediately on the cranial side of the arterial incision to prevent bleeding. Six of these animals were treated with PI-88 (35 mg/kg/day) via miniosmotic pumps (Alzet 2ML2) implanted subcutaneously and seven were implanted with miniosmotic pumps (Alzet 2ML2) containing sterile normal saline (control group). At the end of two weeks the animals were anaesthetised with pentobarbitone, perfused with 10% buffered formalin for 20 minutes and euthanised (pentobarbitone) and the denuded arterial segments (from the point of arteriotomy to the ascending aorta) were removed and processed for histological examination. The formalin fixed tissues were transversely serial sectioned (4 $\mu$M) every 100 $\mu$M and the regions of maximal intimal thickening in the saline (control) group were compared with comparable areas from the PI-88 (treated) group. Analyses of these areas were carried out using a digital image system.

Results

Figure 1:
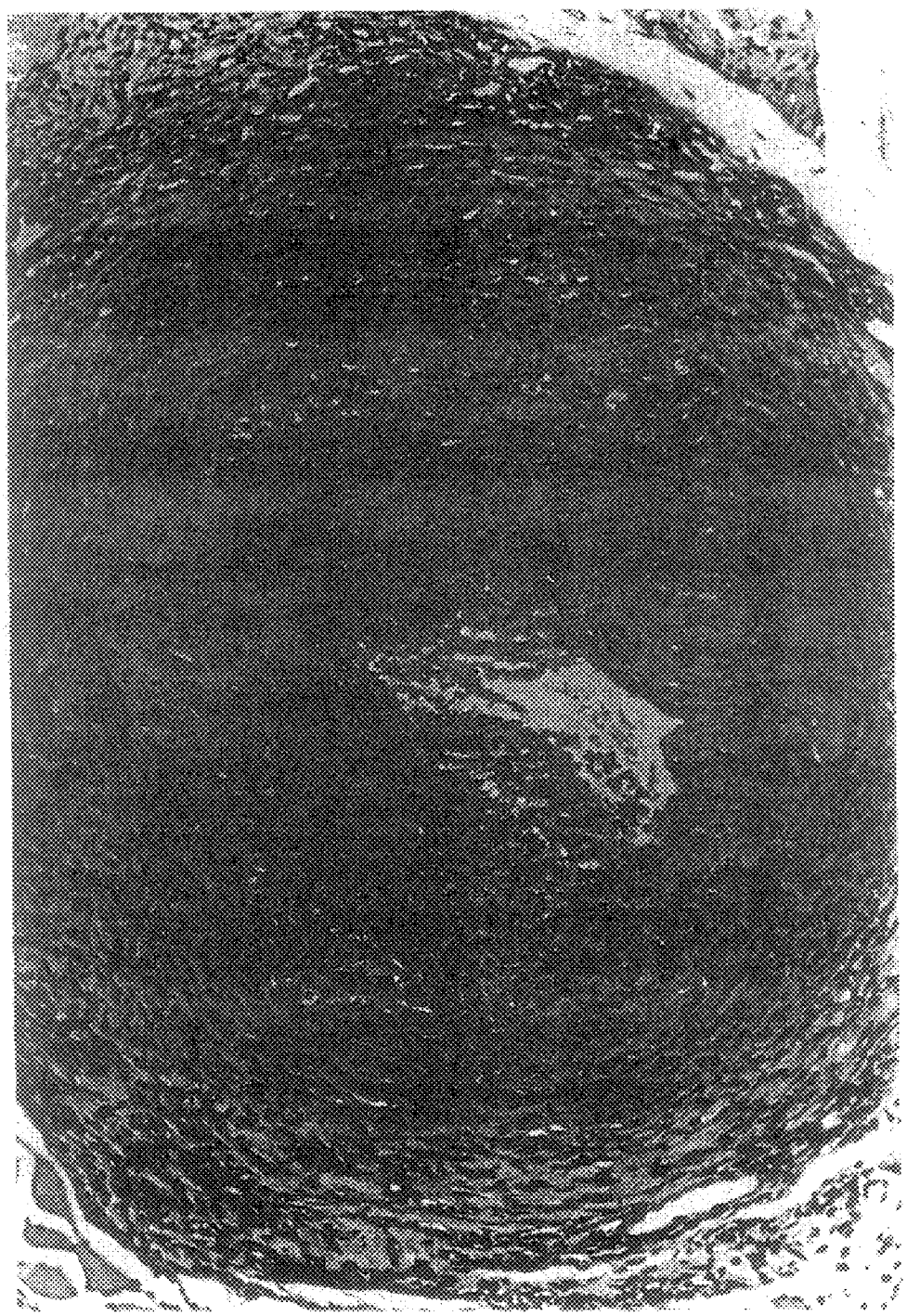
FIG. 1 shows a light microscope view of a haematoxylin and eosin stain of a transverse section of the carotid artery from a rat 14 days after denuding the arterial endothelial cells by saponin treatment. Note that the lumen of the vessel is almost totally occluded by massive smooth muscle cell hyperplasia.
Figure 2:
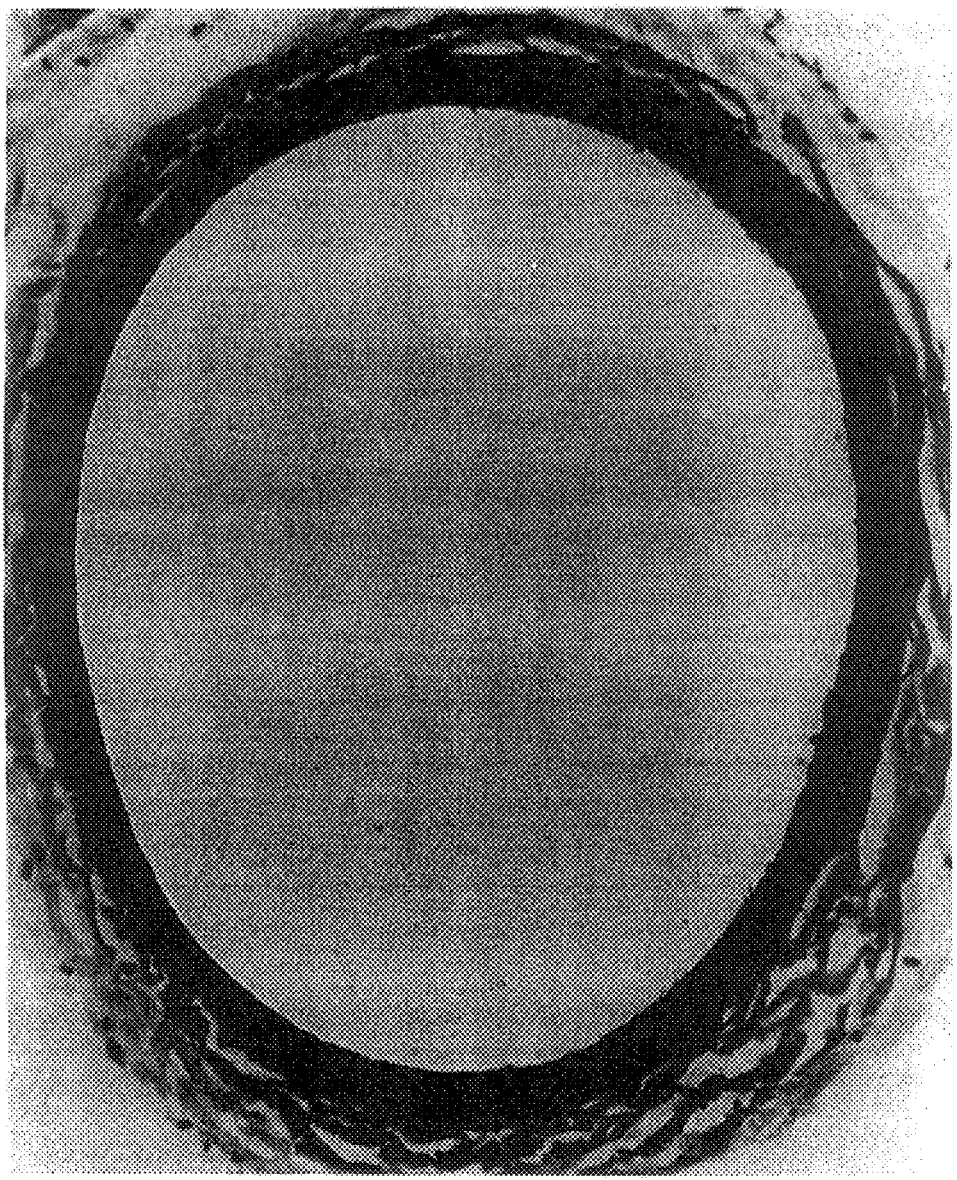
FIG. 2 shows a light microscope view of a haematoxylin and eosin stain of a transverse section of the carotid artery from a normal rat. Note the thin rim of smooth muscle cells lining the vessel wall beneath the vascular endothelium.

The saponin-induced vascular hyperplasia model used in this study is a new procedure which has several important features which should be highlighted. First, brief exposure to the detergent saponin is used to denude the arterial wall of endothelial cells. Such a procedure is similar to the endothelial denudation resulting from balloon angioplasty. Second, massive vascular smooth muscle hyperplasia is observed in the saponin-treated carotid artery 14 days after saponin exposure (FIG. 1) when compared with the carotid artery from an untreated control animal (FIG. 2). In fact, almost complete occlusion of the blood vessel is observed in the saponin-treated vessel (FIG. 1). Third, based on control experiments, the saponin-induced vascular hyperplasia model represents an excellent system for screening of drugs which inhibit vascular hyperplasia, a process which occurs in atherosclerotic plaques and in angioplasty-associated restenosis.

Administration of the sulfated oligosaccharide, sulfated mannopentaose phosphate (PI-88), via miniosmotic pumps (35 mg/kg/day) resulted in a reduction in the saponin-induced vascular hyperplasia (FIG. 3). Histological examination of the carotid arteries from sulfated oligosaccharide treated animals revealed a 34% inhibition of vascular hyperplasia when compared with untreated control animals, an effect which approached significance (P=0.08) (Table 1).

TABLE 1

Ability of Sulfated Mannopentaose Phosphate to Inhibit Smooth Muscle Hyperplasia Induced by Endothelial Denudation.

| Endothelial Denudation Method | Treatment | Arterial Wall Thickness | |
|---|---|---|---|
| | | $\mu$m | % Control |
| Saponin | Saline | 401.8 ± 45.7[a] | 100 ± 11.3 |
| Saponin | PI-88 (35 mg/kg/day) | 266.7 ± 27.7[b] | 66.4 ± 6.9[b] |

[a]Data presented as mean ± SEM
[b]Compared with control, P value = 0.08.

In the second procedure employing the balloon dilation model, the degree of vascular intimal hyperplasia was calculated as a percentage of the total area of the vessel cross-section. Specifically, the percentage of hyperplasia was determined to be the area of the tunica intima divided by the cross-sectional area of the artery. In this experiment, it was found that administration of sulfated mannopentaose phosphate (PI-88), via miniosmotic pumps at a dose of 35 mg/kg/day resulted in a statistically significant (P=0.0008) reduction in vascular intimal hyperplasia (Table 2).

TABLE 2

Ability of Sulfated Mannopentaose Phosphate to Inhibit Smooth Muscle Hyperplasia Induced by Endothelial Denudation.

| Endothelial Denudation Method | Treatment | Percentage of neointima | SEM |
|---|---|---|---|
| Balloon catheter dilation | saline | 57.66 | 3.17 |
| Balloon catheter dilation | PI-88 | 36.02[a] | 3.48 |

[a]Compared with control P = 0.008 (unpaired t-test).

REFERENCES

1. Marcum, J. A., Reilly, C. F. and Rosenberg, R. D. (1986). Prog. Hemost. Thromb. 8:185–215.
2. Castellot, J. J., Wright, T. C. and Karnovsky, M. J. (1987). Semin. Thromb. Hemost. 13:489–503.
3. Karnovsky, M. J., Wright, T. C., Castellot, J. J., Choay, J., Lormeau, J. C. and Petitou, M. (1989). Ann. N.Y. Acad. Sci. 556:268–281.
4. Campbell, J. H., Rennick, R. E., Kalevitch, S. G. and Campbell, G. R. (1992). Exp. Cell Res. 200:156–167.
5. Vlietstra, R. E. and Holmes, D. R. (1988). J. Card. Surg. 3:53–66.
6. O'Brien, E. R., Garvin, M. R., Dev, R., Stewart, D. K., Hinohara, T., Simpson, J. B. and Schwartz, S. M. (1994). Am. J. Pathol. 145:883–894.
7. Schwartz, L. and Seidelin, P. H. (1995). Prog. Cardiovasc. Dis. 38:67–86.
8. Clowes, A. W., Reidy, M. A. and Clowes, M. M. (1983). Lab. Invest. 48:208–215.

What is claimed is:

1. A method for the inhibition of vascular smooth muscle cell hyperplasia in a human or other warm-blooded animal patient in need of such treatment, which method comprises administration to the patient of an effective amount of sulfated mannopentaose phosphate.

2. A method according to claim 1, wherein said sulfated mannopentaose phosphate is prepared by sulfation of mannopentaose phosphate prepared by enzymatic or chemical degradation of a naturally occurring polysaccharide.

3. A method according to claim 2, wherein said mannopentaose phosphate is from the yeast Pichia holstii.

4. A method according to claim 1, wherein the treatment comprises treatment of atherosclerosis or angioplasty-associated restenosis.

5. A method according to claim 3, wherein the treatment comprises treatment of atherosclerosis or angioplasty-associated restenosis.

* * * * *